United States Patent [19]

Nelson, Jr.

[11] 4,267,268

[45] May 12, 1981

[54] SPERMATOZOA EXTENDERS

[76] Inventor: Robert A. Nelson, Jr., 340 Promenade East, #138, Portland, Me. 04101

[21] Appl. No.: 19,308

[22] Filed: Mar. 12, 1979

[51] Int. Cl.$^3$ ............................................... A01N 1/02
[52] U.S. Cl. ........................................................ 435/2
[58] Field of Search ........................... 195/1.8; 424/105

[56] References Cited

PUBLICATIONS

Fukuhara et al.,–Chem. Abst., vol. 79 (1973) p. 134,684r.

Primary Examiner—Frederick E. Waddell

[57] ABSTRACT

Extenders for spermatozoa are obtained from porcine seminal plasma and are useful in connection with increasing motility and fertility of porcine sperm as well as extending the useful number of treatments of a sperm-containing solution. Additional extenders are selected from the class consisting of a pyruvate and an oxaloacetate. Another extender having a physiochemical effect can be admixed with the oxaloacetate, pyruvate and/or porcine seminal plasma extenders and can have a synergistic effect therewith.

10 Claims, 1 Drawing Figure

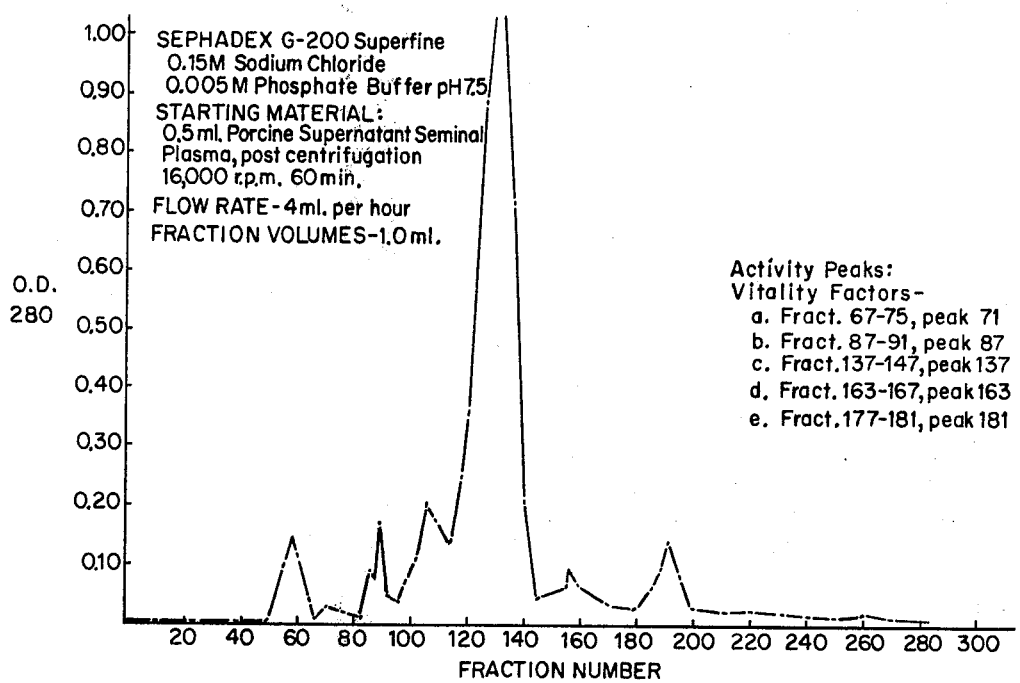

SPERMATOZOA EXTENDERS

BACKGROUND OF THE INVENTION

The maintenance of spermatozoa outside the body of man and animals is customarily carried out in artificial insemination procedures. There are a variety of materials and procedures which are used in the prior art to prolong the survival of spermatozoa outside the body and/or to enable a single sperm-containing ejaculate to be diluted so as to be useful to impregnate a large number of females. Many of these materials and procedures are limited as to the extent they can prolong survival. Materials more complex than the ordinary balance solutions are commonly referred to as "extenders."

There is a particular problem with prolonging the survival of porcine spermatozoa. In many cases, the survival of washed porcine sperm is limited to only 2 to 4 hours at physiological conditions. Attempts to freeze porcine sperm by conventional techniques have been relatively unsuccessful. Often recovery of less than 20% of motility of the spermatozoa is obtained. Glycerol which is often considered essential for successful freezing of bovine spermatozoa can be highly toxic to porcine boar sperm.

The admixture of either washed or unwashed porcine spermatozoa with any of a variety of commercially available extenders usually results in two dramatic effects. After only a few hours the sperm show progressively decreasing motility. In addition, they agglutinate or clump to one another or to the particulate material normally present in seminal fluid and which is difficult to remove from the spermatozoa by filtration or differential centrifugation.

Often extenders used for extending porcine spermatozoa, are only effective to allow the seminal plasma of boars to be diluted as with egg yolk. Thus an ejaculate from a boar can be extended by some commercial extenders to allow 6 to 8 sows to be inseminated. However, the life of the sperm is often not extended by commercially available extenders. Thus often in many species, commercial extenders don't extend the life span of the spermatozoa but only permit survival of diluted sperm equivalent to those of undiluted sperm.

It has long been recognized that it would be useful to have an extender which extends both the fertility and motility of pig and other sperm while allowing dilution of the sperm to a high degree to enable a single ejaculate to be used for insemination of an increased number of sows.

SUMMARY OF THE INVENTION

It is an important object of this invention to provide extenders for spermatozoa, which can be used individually or in combination to permit high dilutions of sperm and preferably increase the time span of motility and fertility of sperm.

It is still another object of this invention to provide extenders in accordance with the preceding object which are particularly useful in connection with porcine artificial insemination.

Still another object of this invention is to provide a method of obtaining extenders from porcine seminal plasma and avoiding factors toxic to spermatozoa in such plasma.

According to the invention, an aqueous spermatozoa-containing solution has incorporated therein an extender selected from the class consisting of a pyruvate and an oxaloacetate and mixtures thereof. Preferably the aqueous solution further contains a physiochemical protective agent for preventing osmotic shock which agent is preferably gelatin.

Other useful extenders are provided in accordance with this invention for use solely in porcine artificial insemination. These extenders are provided in a solution which comprises at least one extender which acts to prolong motility and fertility of porcine spermatozoa, is obtainable from porcine seminal fluid and contains five protein materials from the class consisting of a porcine seminal fluid protein having a molecular weight of about 800,000, another protein having a molecular weight of 250,000, another protein having a molecular weight of 30,000, another protein having a molecular weight of 10,000, and another protein having a molecular weight of 9,000 and mixtures thereof. Preferably all of these extenders are used together. In a preferred form, the protein material extenders are a mixture of extenders obtained directly in porcine seminal ejaculate collected after first discarding an initial portion which has been found to contain a toxic factor.

Preferably the five extenders obtained from porcine seminal plasma are used together along with a pyruvate or oxaloacetate and a physiochemical osmotic shock preventative such as gelatin in a sperm extender mixture for porcine sperm. The mixture is believed to have a synergistic effect in extending the fertility and motility periods of porcine sperm. The advantageous effects of the pyruvate, oxaloacetate, gelatin and mixtures thereof are useful in connection with spermatozoa of all kinds and can have useful effects on spermatozoa of birds, beef, chicken and other mammalian and avian species of various types.

It is a feature of this invention that the extenders of this invention not only permit dilution of sperm solutions but also extend life and specifically motility and fertility. Thus the extenders are sometimes herein called "vitality factors."

BRIEF DESCRIPTION OF THE DRAWINGS

The above and other objects, features and advantages of the present invention will be better understood from the present specification when read in conjunction with the attached drawing of a graph indicating vitality factors found to be present in a porcine seminal fluid from which spermatozoa and other material have been removed.

DESCRIPTION OF PREFERRED EMBODIMENTS

A first type of extender which is used both to permit dilution of sperm solutions and to extend the fertility and motility in accordance with the present invention is a pyruvate, oxaloacetate or mixture thereof. These materials are essential for carbohydrate metabolism. It is believed that use of one or both of the extenders enables sperm to carry out metabolism longer, thus lengthening the time of motility and fertility.

The pyruvate and oxaloacetate used can be sodium pyruvate, potassium pyruvate, calcium pyruvate, sodium oxaloacetate, potassium oxaloacetate, calcium oxaloacetate, ammonium oxaloacetate and other metals of these materials which are not harmful to sperm. Preferably when admixed with sperm they are used in total molar concentrations in aqueous solutions of from 0.05 molar to 0.005 molar with about 0.01 molar solutions being preferred. Above 0.05 molar, a toxic effect is sometimes exhibited while below 0.005 molar little or no effect is exhibited.

The solutions in which the materials are mixed can be aqueous solutions of various types. Preferably the materials are added to seminal plasma although they can be premixed in buffered solution having a physiological pH as for example pH 7.4. Veronal buffer is a preferred diluent for the pyruvate and/or oxaloacetate. Solutions within the ranges recited can be added to ejaculate of sperm-rich porcine seminal fluid to 20 times the dilution of the original seminal fluid with the advantages of this invention being present. Often it is found that the life, that is, motility and fertility of porcine sperm is increased to 10 or more times the 1 to 3 hours of normal vitality of sperm in seminal ejaculate of pigs when the additives of this invention are used.

Preferably a small amount of gelatin as for example about 0.5 to 1.0% by volume of the final admixture with a sperm-containing aqueous solution is used, in combination with the pyruvate and/or oxaloacetate. The gelatin has a physiochemical effect and acts to prevent osmotic shock of the sperm and is useful to give further extension and increased vitality in extenders of the present invention. The gelatin can be admixed in any physiologically buffered aqueous solution nondamaging to sperm as for example veronal buffer at a pH of about 7.4.

The gelatin can be bovine, porcine or any gelatin prepared as known in the art and as for example defined in the *Merck Index* 7th Edition 1960 published by Merck and Co. of Rahway, N.J., pages 473, 474.

The extender obtained from porcine seminal plasma is in aqueous solution and can be a part of the plasma from which spermatozoa and highly viscous milky material have been removed. The supernatant plasma as it will be called in this application has surprisingly been found to contain five factors which prolong motility of spermatozoa in vitro and extend fertility and can be considered vitality factors useful as extenders for porcine spermatozoa. It has also been found that there is at least one toxic factor present in seminal ejaculate of boars which is found in the first portion of the ejaculate and can be discarded with the remainder of the ejaculate used for providing the extenders of this invention. The five vitality factors which enhance the motility of washed spermatozoa in vitro are found to be protein materials having molecular weights of 800,000, 250,000, 30,000, 10,000 and 9,000. The 9,000 molecular weight factor is the major vitality factor in porcine seminal plasma and far surpasses the other vitality factors in biological activity per weight unit. Each of the factors can act to increase vitality of porcine sperm alone but are preferably used in combination to obtain maximized increase in vitality and ability to permit greater dilutions of sperm.

In obtaining the five vitality factors, it is preferred to discard about the first 25 ml of pre-sperm-rich ejaculate in order to avoid a naturally occurring toxic factor which tends to agglutinate or kill the sperm. The remainder is collected and normally amounts to about 150 to 250 millimeters and contains the desired vitality factors in the fraction of the ejaculate known as the post sperm-rich portion.

While the five vitality factors could be suspended in veronal buffer or other physiological buffered aqueous solution, it is preferred to obtain and use them directly in porcine seminal plasma.

In a typical example of obtaining the five vitality factors for use in porcine artificial insemination in accordance with this invention, seminal plasma is hand-collected from a trained boar mounted on a dummy. The first 25 ml containing high concentration of toxic factor is discarded. The remaining ejaculate, usually 150 to 250 ml is then passed through a 4-inch by 4-inch surgical gauze to remove gross impurities and collected into a pre-warmed 250 ml thermos bottle maintained at room temperature. Microscopic examination for sperm count and morphology including presence of erythrocytes can then be done. Samples contaminated with blood are discarded. Samples contaminated with bacteria are also discarded. The ejaculate is then slowly cooled to room temperature.

In a second step, the material is centrifuged at 1500 rpm for 15 minutes to harvest the spermatozoa for other uses. The time and degree of centrifugation can vary. The remaining seminal fluid can be cooled to 5° C. or can be frozen at $-20°$ C. until ready for further processing.

In further processing, the seminal plasma preferably at about 5° C. to 0° C. is centrifuged at 15,000 rpm for 60 minutes. The time and degree of spinning can vary. The purpose of this centrifugation is to remove the viscous milky white material believed to be a polysaccharide and which can also contain materials toxic to sperm. The supernatant fluid can be refrozen for several days, thawed and centrifuged again to remove any flocculent material. If used immediately, no additional centrifugation need take place.

This supernatant seminal plasma is found to contain the five vitality factors of this invention. They can be directly used as by adding the supernatant fluid directly to a sperm-containing ejaculate, adding washed sperm to the seminal fluid or forming the aqueous mixtures with live sperm-containing mixtures. The supernatant fluid can be used to dilute sperm ejaculates in dilutions of from 1:10 to 1:50 to extend the sperm ejaculate in terms of volume and also to prolong the motility and fertility of such sperm.

The exact degree of dilution of the vitality factors of the present invention with sperm can vary greatly. They are used in a dilution such that they have a vitality prolonging effect on the spermatozoa.

The vitality factors may be separated from other constituents of seminal plasma by any one of at least four techniques. Although these factors are relatively heat stable, the procedures are performed at 5° C. in order to prevent denaturation or autolysis of other constituents and to minimize the risk of microbial contamination. The most convenient method to employ as a first step consists of passing the supernatant plasma through gel to separate the constituents on the basis of molecular weight. Similarly, "salting out" using either $Na_2SO_4$ or $(NH_4)_2SO_4$ is convenient, but frequently it is difficult to detect three of the five "vitality factors." Lastly, the major components can be recovered following separation by ionic charge differences by chromatography using either DE-52 or CM-52 cellulose or by isoelectric focusing using columns or ampholines supported in a gel bed.

In preparation by gel filtration, columns containing Sephadex G100 or G200, superfine porosity, are generally employed for the initial isolation. Ultrogel ACA 44 or 54 can be substituted since more material can be employed and more rapid flow rates used. These methods involve passage of the semen through columns which have been preequilibrated with physiologic salt solution, i.e., 0.15 M NaCl buffered at pH 7.5 with 0.005 M phosphate. The factors pass through the column at different rates from one another and from other macro molecules and, hence, may be isolated in a relatively pure state. A specific example is described below:

EXAMPLE I

Approximately 0.5 ml of cold porcine supernatant plasma obtained as described above was applied to a 2.5×45 cm. glass column containing Sephadex G200 preequilibrated with 0.15 M NaCl/0.005 M phosphate. The flow rate was adjusted to 4 ml per hour. Approximately 1.0 ml fractions were collected using an Isco fraction collector. Three hundred fractions were collected. Six major protein peaks were found when individual fractions were examined in a spectrophotometer at 280 m$\mu$. Five activity peaks were located corresponding to molecular weights of 800,000, 250,000, 30,000, 10,000 and 9,000, respectively. The reactivity of the fraction containing the 9,000 molecular weight factor was quite dramatic in that washed spermatozoa survived for several days in a media containing only 0.01 M sodium pyruvate and veronal buffer pH 7.5, containing calcium and magnesium. Survival of washed spermatozoa was enhanced over controls but ordinarily less than 8 hours with the other vitality factors. When sodium pyruvate is used alone some degree of enhancement is obtained. When sodium oxaloacetate alone or admixed with sodium pyruvate is used enhancement of motility and fertility is obtained.

In preparation by "salting out," when large quantities of supernatant plasma are available, it has been found convenient to partially purify and concentrate the factors by a preliminary differential precipitation using either $Na_2SO_4$ or $(NH_4)_2SO_4$. Solutions of 4.0 M salt are adjusted to pH 6.0 and slowly added stepwise to the supernatant porcine seminal plasma, which are also adjusted to pH 6.0, to yield final concentrations of 2.0, 2.5, 3.0 and 3.5 M. All procedures are performed at 5° C. After each step, the precipitate is removed and washed once by centrifugation in salt of the appropriate concentration. Each precipitate then is solubilized in 0.15 M NACl containing 0.005 M phosphate buffer, pH 7.5. The sulfate salt is then removed by dialysis against 0.15 M NaCl/0.005 M phosphate or by passage of the solutions through a small column containing Sephadex G-25.

In preparation by cellulose chromatography, either the initial step in purification or additional purification following filtration through gel or "salting out" may be accomplished by ion exchange chromatography using a basic anion exchanger, e.g., diethyl amino ethyl cellulose or an acidic ion exchanger, e.g., carboxymethyl cellulose. A typical example follows:

EXAMPLE II

Diethyl aminoethyl cellulose, DE-52, microgranular grade, was washed thoroughly and equilibrated with degassed 0.01 M NaCl containing 0.005 M phosphate buffer, pH 7.5. Then it was used to pack a 2.5×50 glass column and washed with the same buffer in the cold at 5° C. for 18 hours. At the same time, 30 ml of porcine supernatant plasma was dialyzed against the low ionic strength buffer overnight in the cold. A very fine white precipitate was removed by centrifugation at 15,000 rpm for 60 minutes. Approximately 30 ml of the supernatant fluid was applied to the column followed by the 0.01 M NaCl/0.005 phosphate buffer. The column was washed for about 24 hours with this buffer and then eluted in a straight line gradient using 750 ml each of 0.01 M NaCl/0.005 M phosphate and 0.30 M NaCl/0.005 M phosphate. The ionic strength of fractions was measured using a conductivity meter manufactured by Radiometer Copenhagen. The ionic strength of the fractions was then adjusted to 0.15 M by addition of an appropriate amount of exactly 3.0 M NaCl. Fractions above 0.15 M were adjusted by addition of the appropriate amount of 0.005 M phosphate buffer only. The major protein in the porcine supernatant plasma flowed directly through this column indicating an almost complete absence of negative charges. Approximately 90% of the 9,000 molecular weight vitality factor appeared in the overnight wash. It did not pass directly through the column but was delayed apparently due to some weak positive charges on the molecule. The four other vitality factors could not be detected on this column. There was no detectable toxic factor in the material applied to the column.

In an example of preparation by isoelectric focusing, five ml of porcine supernatant plasma was dialyzed in the cold first against 500 ml of 0.005 M phosphate buffer for 18 hours and then against another 500 ml of 0.005 M phosphate buffer for about 6 hours. About 2 ml then was mixed with a precooled mixture of ampholine resins, pH 4 to 10, and sucrose prepared exactly as outlined in Instruction Manual 8100, prepared by LKB Produkter. The mixture was then poured into a 110 ml column equipped with a water jacket connected to a 0° C. water bath. The electrode solutions were added, the column was sealed and then subjected to a charge of 1000 volts for 48 to 72 hours. After the current was turned off, the column was emptied slowly by gravity flow. Approximately 1 ml samples were collected. Each fraction was adjusted to 0.15 M by the addition of an appropriate volume of exactly 3.0 M NaCl. The pH was adjusted to 7.5 by the addition of an appropriate volume of 2 M tris buffer, pH 7.5, or, near the ends of the scale, of either 0.1 M NaOH or 0.1 M HCl. Only one potent "vitality factor" could be located on this column in fraction around pH 8.2.

The most convenient and practical method for isolating the five vitality factors from porcine supernatant plasma involves molecular sieving, i.e., passage of the material through a gel which separates the factors from one another and from other constituents by molecular size and/or weight. Two commercial preparations of gel have proved satisfactory, i.e., Sephadex of porosities coded G-200 or G-100, manufactured by Pharmacia Fine Chemicals, and Ultrogel of porosities coded ACA 44 or 34, manufactured by LKB-Producter. The major advantage of these gels concerns the fact that they separate the five vitality factors which have a strikingly different span of molecular weights ranging from 800,000 to 9,000. A detailed outline of results obtained with Sephadex G-200 and post-sperm-rich supernatant plasma is shown in graphic form in the FIGURE.

Similar results may be obtained more easily when Sephadex G-100 or Ultrogel 34 is used as in the following specific example:

EXAMPLE III

Reagent grade Sephadex G-100, superfine porosity, is equilibrated for two days in a solution of 0.15 M sodium chloride containing 0.005 M phosphate buffer, pH 7.5. The gel solution is degassed by means of a vacuum pump or a water gasket vacuum for two to three hours. The gel is then poured to fill a 10×120 cm. glass column at room temperature. The 0.15 M NaCl/0.005 M phosphate then is used to wash and equilibrate the column overnight at room temperature. The column is then transferred to a cold room at 5° C. and again washed and equilibrated with cold saline-phosphate buffer. About 100 ml of precooled post-sperm-rich supernatant plasma then is applied by means of a gravity siphon. The flow rate is maintained at 40 ml per hour. After application of the supernatant plasma the column is eluted or washed with the saline-phosphate buffer for from four to six days until all plasma constituents have passed through the column. Throughout the entire procedure an Isco fraction collector is used to collect 40 ml fractions of eluate. After appropriate testing of individual fractions, pools of the active components are made and frozen at −75° C.

Three methods are employed to monitor the sequence of elution of the constituents of the supernatant plasma. First, measurements of the optical density at 280 m$\mu$ are made continuously during elution by means of a spectrophotometer with a photo cell placed between the outlet of the column and the fraction collector. Second, assays for serum constituents are made by immunodiffusion assays with commercially available anti-hog serum constituents. Immunodiffusion assays for specific constituents of hog semen are made with new antisera made in this laboratory. Third, assays for the vitality factors and for the possible presence of toxic factor are performed as outlined below:

Spermatozoa are freshly collected from a suitable boar and diluted 1/10 in veronal buffer containing calcium and magnesium at 35° C. The portion to be used for assay of the vitality factors is washed twice in the veronal buffer by centrifugation and resuspension at 35° C. The portion to be assayed for any toxic factors also is washed twice but veronal buffer containing 0.005 M sodium pyruvate is used. These washed suspensions are then dispensed into small tubes containing dilutions of the test fractions in isotonic veronal buffer. Ordinarily, 0.25 ml of washed spermatozoa and of dilutions of the fractions are employed. These mixtures are incubated for four hours at 35° C. with intermittent mixing "by hand." Microscopic readings of the percent motility of 50 spermatozoa are performed at hourly intervals. Since spermatozoa in the control for vitality factor were washed and suspended in veronal buffer alone, the percentage surviving usually declines dramatically in one to two hours. Fractions from the column which promote survival of 80 to 90 percent for three to four hours indicate significant levels of one of the five vitality factors. On the other hand, since spermatozoa in the control for toxic factor were washed and resuspended in veronal buffer containing 0.005 M sodium pyruvate, usually about 70 to 90 percent of the spermatozoa are actively motile after four hours at 35° C. Fractions from the column which decrease motility to less than 25% are interpreted as containing a toxic factor. There is a broad spectrum of physiochemical variations which may be employed to isolate the five protein vitality factors from porcine seminal plasma. Preparative electrophoresis has been attempted but with limited success. The presently described methods have proved to be the most practical and convenient. Nonetheless there are several tolerated variations in the isolation procedures and methods for potency measurement which may be summarized as follows:

(a) Types of gel or cellulose. Reasonably good results may be obtained when G-200 superfine, G-200 fine, G100 fine, G-75 superfine or G-75 fine are substituted for G-100 superfine. Similarly, Ultrogel ACA 34 or 44 may be employed with satisfactory results. DEAE cellulose, granular or DEAE-Sephadex may be substituted for DE-52, microgranular grade. Also, CM cellulose, granular or CM-Sephadex may be used instead of CM-52, microgranular grade.

(b) Size of columns. Essentially the same results have been obtained in terms of sequence of elution and relative purity, but often one or two factors have not been detectable, presumably due to their lower concentration in individual samples of seminal plasma, when procedures were performed with columns measuring 2.5×45 cm, 2.5×95 cm and 5.0×60 cm. It is important to emphasize that the total amount of seminal plasma applied to the column must not exceed the binding capacity of the cellulose employed and that the volume applied to a gel column must be limited to an amount that permits separation of the factors as they flow through any individual bed volume.

(c) Temperature. Columns may be used at room temperature and the sequence of elution of plasma constituents remains the same. However, porcine seminal plasma usually contains bacterial contamination when it is obtained by the usual techniques and buffers containing 50 mg per liter of Gentocin, manufactured by Schering Corporation, have been used. In addition, there is a danger of deterioration or autolysis of the vitality factors as well as other constituents of the seminal plasma.

(d) Time. The times recommended for dialysis, fractionation and flow rate are near optimal but are not critical in isolating the products described. Dialysis may be performed for shorter times by changing the buffer more frequently. More rapid flow rates may be employed, especially with the DE-52 and CM-52 cellulose columns. Reasonably satisfactory separation may be achieved with Sephadex or Ultrogel columns when considerably more rapid flow rates are employed.

(e) Buffers. Column chromatography with DE-52 cellulose will give approximately the same results when either phosphate or tris buffer of different concentrations, but preferably at pH 7.0 to 8.0, are employed. Similarly, acetate or other buffers from pH 5.0 to 6.0 may be used with CM-52. Procedures involving gel filtration may be performed at pH 7.0 to 8.0.

The following are specific examples of extenders of this invention:

EXAMPLE IV

A supernatant seminal plasma is obtained by collecting pooled porcine ejaculate from 10 boars. The first 25 ml of each specimen as collected is discarded. After gentle centrifugation of each specimen at 3000 rpm for 15 minutes to remove sperm and 15,000 rpm for 60 minutes to remove a viscous milky white material the supernatant seminal plasma is pooled and diluted to 15 times its original volume with veronal buffer to form a useful extender for porcine seminal fluid. Alternately washed sperm can be resuspended in the diluted seminal plasma. Sperm have increased motility and fertility as opposed to similar sperm not admixed with the extender of this invention. The veronal buffered aqueous solution of seminal plasma can be added in an amount of 850 ml to 150 ml of freshly collected boar ejaculate and is found to increase motility, fertility over a several hour period.

When the resulting solution is adjusted to 0.01 M sodium pyruvate or sodium oxaloacetate and from 0.5 to 1.0% by volume gelatin even greater time of motility and fertility are obtained.

While specific examples have been shown and described, many variations are possible. It should be understood that some seminal plasma may be more or less rich in the vitality factors of this invention and thus pooled plasma is preferred for use. Similarly, the vitality effect of plasma may vary depending upon the particular sperm involved. Thus specific volumes, concentrations and the like can vary greatly. In all cases, not only is greater dilution of sperm possible to enable impregnation of a large number of females, but preferably the length of time of motility and fertility is greatly increased without undesirable side effects or damage to the sperm.

What is claimed is:

1. A solution for use in porcine artificial insemination, said solution comprising an extender which acts to prolong motility and fertility of porcine sperm before or after dilution of said sperm, is obtainable from porcine seminal fluid and contains a protein material extender selected from the class consisting essentially of a porcine seminal fluid protein having a molecular weight of about 800,000, a porcine seminal fluid protein having a molecular weight of about 200,000, a porcine seminal fluid protein having a molecular weight of about 30,000, a porcine seminal fluid protein having a molecular weight of about 10,000, a porcine seminal fluid protein having a molecular weight of about 9,000, and mixtures thereof.

2. A solution in accordance with claim 1 wherein said protein material has a molecular weight of about 800,000 and acts to extend the motility and fertility of porcine spermatozoa when said spermatozoa are diluted in aqueous media at dilutions corresponding up to 20 times the normally occurring dilution of sperm in seminal fluid.

3. A solution in accordance with claim 1 wherein said protein material has a molecular weight of about 200,000 and acts to extend the motility and fertility of porcine spermatozoa when said spermatozoa are diluted in aqueous media at dilutions corresponding up to 20 times the normally occurring dilution of sperm in seminal fluid.

4. A solution in accordance with claim 1 wherein said protein material has a molecular weight of about 30,000 and acts to extend the motility and fertility of porcine spermatozoa when said spermatozoa are diluted in aqueous media at dilutions corresponding up to 20 times the normally occurring dilution of sperm in seminal fluid.

5. A solution in accordance with claim 1 wherein said protein material has a molecular weight of about 10,000 and acts to extend the motility and fertility of porcine spermatozoa when said spermatozoa are diluted in aqueous media at dilutions corresponding up to 20 times the normally occurring dilution of sperm in seminal fluid.

6. A solution in accordance with claim 1 wherein said protein material has a molecular weight of about 9,000 and acts to extend the motility and fertility of porcine spermatozoa when said spermatozoa are diluted in aqueous media at dilutions corresponding up to 20 times the normally occurring dilution of sperm in seminal fluid.

7. A solution in accordance with the solution of claim 1 and further comprising a fertility and motility extending amount of an additional extender selected from the class consisting essentially of a pyruvate and an oxaloacetate and mixtures thereof.

8. An extender for prolonging the motility and fertility of porcine sperm in vivo,
said extender comprising seminal fluid of at least one boar collected after discarding a first portion containing a toxic factor and from which sperm and a viscous milky material have been removed to leave at least one vitality factor, said seminal fluid being present in an amount of from 10 to 30% by volume with an aqueous media.

9. A method of obtaining an extender for prolonging motility and fertility of porcine sperm in vivo,
said method comprising collecting the ejaculate of a boar after discarding a first portion thereof containing a sperm toxic factor,
removing a viscous milky material from said ejaculate,
and utilizing said ejaculate as a mixer with porcine sperm in aqueous solution.

10. A method in accordance with claim 9 and further comprising
incorporating an additional extender therewith selected from the group consisting essentially of a pyruvate, an oxaloacetate and mixtures thereof.

* * * * *